United States Patent [19]

Bagli

[11] Patent Number: 4,507,304

[45] Date of Patent: Mar. 26, 1985

[54] USE OF 6-AMINO-5-PYRIMIDINECARBONITRILE DERIVATIVES AS CARDIOTONIC AGENTS

[75] Inventor: Jehan F. Bagli, Kirkland, Canada

[73] Assignee: American Home Products Corporation, New York, N.Y.

[21] Appl. No.: 509,887

[22] Filed: Jun. 30, 1983

[51] Int. Cl.$^3$ .......................................... A61K 31/505
[52] U.S. Cl. ................................................ 514/269
[58] Field of Search ......................... 424/251; 544/319

[56] References Cited

U.S. PATENT DOCUMENTS

| 4,072,746 | 2/1978 | Lesher et al. | 424/263 |
| 4,313,951 | 2/1982 | Lesher et al. | 424/263 |

FOREIGN PATENT DOCUMENTS

| 72790 | 5/1970 | German Democratic Rep. | 424/263 |
| 101894 | 11/1973 | German Democratic Rep. | |
| 46-08698 | 3/1971 | Japan | 424/263 |
| 7176981 | 10/1982 | Japan | 424/263 |
| 7210637 | 2/1973 | Netherlands | 424/263 |
| 1189188 | 11/1966 | United Kingdom | 424/263 |

OTHER PUBLICATIONS

S. Kisaki et al., Chem. Pharm. Bull., 22, 2246, (1974).
A. Kumar et al., Synthesis, (9), 748, (1980).

*Primary Examiner*—Albert T. Meyers
*Assistant Examiner*—John W. Rollins, Jr.

[57] ABSTRACT

Herein is disclosed a method of using 6-amino-5-pyrimidinecarbonitrile derivatives, therapeutically acceptable addition salts thereof, for increasing cardiac contractility in a mammal.

6 Claims, No Drawings

USE OF 6-AMINO-5-PYRIMIDINECARBONITRILE DERIVATIVES AS CARDIOTONIC AGENTS

BACKGROUND OF THE INVENTION

This invention relates to a method of using 6-amino-5-pyrimidinecarbonitrile derivatives, or a therapeutically acceptable addition salt thereof, as cardiotonic agents for increasing cardiac contractility in a mammal and to pharmaceutical compositions thereof.

Related hereto is my patent application Ser. No. 509,886 filed on even date herewith.

A number of pyrimidines are described, for example, B. Rogge et al., Chem. Abstr. 81, 25691 m (1974) for East German Pat. No. 101,894, Nov. 20, 1973; S. Kisaki et al., Chem. Pharm. Bull., 22, 2246 (1974); Derwent Publications Ltd., Farmdoc 6245W for German Offenlegenshift No. 2,410,650, published Sept. 11, 1975; Derwent Publications Ltd., Farmdoc 05783J for Japanese Pat. No. 7,176,981, published Oct. 10, 1982; Derwent Publications Ltd., Farmdoc 10368U for Netherland Pat. No. 7,210,637, published Feb. 6, 1973; Chemical Abstracts, 75, 49129 m (1971) for Japanese Pat. No. 7,108,698, published Mar. 5, 1971; A. Kumar et al., Synthesis, (9), 748 (1980); and Derwent Publications Ltd., Farmdoc 31812R for British Pat. No. 1,189,188, published Nov. 9, 1966. In addition, a number of cardiotonic pyridinones are described by G. Y. Lesher et al., U.S. Pat. No. 4,072,746, Feb. 7, 1978 and G. Y. Lesher et al., U.S. Pat. No. 4,313,951, Feb. 2, 1982.

Most of the 6-amino-5-pyrimidinecarbonitrile derivatives used in this invention are described by Derwent Publications Ltd., Farmdoc 46076R for East German Pat. No. 72,790, published May 5, 1970 as chemical intermediates for the production of physiologically active substances.

SUMMARY OF THE INVENTION

According to the present invention, a method is provided for increasing cardiac contractility in a mammal by administering to the mammal an effective cardiotonic amount of a compound of formula I

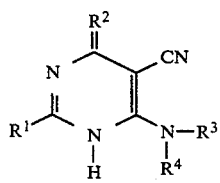

in which $R^1$ is lower alkyl, cyclo(lower)alkyl or benzyl; $R^2$ is oxo or thioxo; $R^3$ is hydrogen or lower alkyl; and $R^4$ is lower alkyl; or a therapeutically acceptable addition salt thereof.

A preferred group of compounds for increasing cardiac contractility is represented by formula I in which $R^1$ is lower alkyl, cyclo(lower)alkyl or benzyl; $R^2$ is oxo; $R^3$ is hydrogen; and $R^4$ is lower alkyl.

A pharmaceutical composition is obtained by admixing the compound of formula I or a therapeutically acceptable addition salt thereof with a pharmaceutically acceptable carrier.

DETAILED DESCRIPTION OF THE INVENTION

The term "lower alkyl" as used herein means straight and branched chain alkyl radicals containing from one to six carbon atoms, preferably one to four carbon atoms, and includes methyl, ethyl, propyl, 1-methylethyl, butyl, 1,1-dimethylethyl, pentyl and the like, unless stated othewise.

The term "cyclo(lower)alkyl" as used herein means saturated cyclic hydrocarbon radicals containing from three to six carbon atoms and includes cyclopropyl, cyclobutyl, cyclopentyl and cyclohexyl.

The compounds of this invention are capable of forming acid addition salts with therapeutically acceptable acids. THe acid addition salts are prepared by reacting the base form of the appropriate compound of formula I with one or more equivalents, preferably with an excess, of the appropriate acid in an organic solvent, for example, diethyl ether or an ethanoldiethyl ether mixture.

These salts, when administered to a mammal, possess the same pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula I are also capable of forming addition salts with sodium or potassium. These salts are prepared by reacting the compounds of formula I with one or more equivalents of sodium or potassium, or a strong base of sodium or potassium, for example, sodium hydroxide, potassium t-butoxide, sodium hydride and the like. These salts, like the acid addition salts, when administered to a mammal possess the same pharmacological activities as the corresponding nonsalt compound of formula I.

The compounds of formula I or a therapeutically acceptable addition salt thereof are useful as cardiotonic agents for increasing cardiac contractility in a mammal. The cardiotonic effect is demonstrated in standard pharmacological tests, for example, in causing an increase in the contractile force of the isolated cat papillary muscle and reversal of pentobarbital-induced cardiac failure in the dog.

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulationed by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as cardiotonic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective cardiotonic amount of the compounds for oral administration can usually range from about 0.05 to 50 mg per kilogram body weight per day in single or divided doses although as aforementioned variations will occur. However, a dosage level that is in the range of from about 0.2 to 20 mg per kilogram body weight per day in single or divided doses is employed most desirably for oral administration in order to achieve effective results.

The compounds of formula I are prepared in the following manner.

Most of the compounds of formula I in which $R^2$ is oxo can be prepared by following the procedure described by Derwent Publications Ltd., Farmdoc 46076R, cited above.

Alternatively, the following reaction scheme illustrates a preferred method for preparing the compounds of formula I.

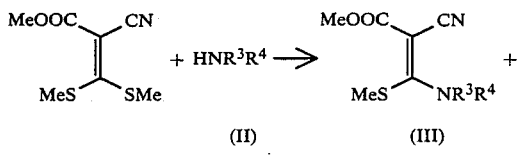

(II)         (III)

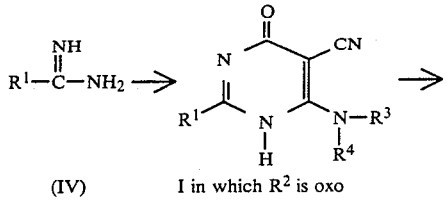

(IV)   I in which $R^2$ is oxo

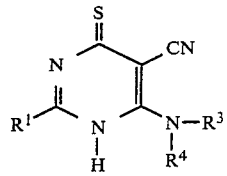

I in which $R^2$ is thioxo

With reference to the above reaction scheme, the bis(methylthio)propenoic acid starting material is reacted with the amine of formula II in which $R^3$ and $R^4$ are as defined herein to obtain the corresponding aminopropenic acid compound of formula III in which $R^3$ and $R^4$ are as defined herein. For this reaction, about equal molar amounts of the above two reagents are allowed to react at about 20° to 40° C. for about ten minutes to two hours in an inert organic solvent, preferably dimethoxyethane, and the compound of formula III is isolated.

Condensation of the compound of formula III in which $R^3$ and $R^4$ are as defined herein with the amidine of formula IV in which $R^1$ is as defined herein gives the corresponding compound of formula I in which $R^1$, $R^3$ and $R^4$ are as defined herein and $R^2$ is oxo. When conducting this condensation, about equal molar amounts of the compounds of formula III and IV are condensed at about 75° to 130° C. for about 20 to 30 hours in an inert organic solvent, preferably dimethylformamide.

To convert the compound of formula I in which $R^1$, $R^3$ and $R^4$ are as defineld herein and $R^2$ is oxo to the corresponding compound of formula I in which $R^1$, $R^3$ and $R^4$ are as defined herein and $R^2$ is thioxo, the following chemical reactions are required. In the first step, the sodium salt of the compound of formula I in which $R^2$ is oxo is reacted with an excess of phosphorous oxychloride at about 90° to 120° C. for about one to five hours to obtain the corresponding 4-chloro-5-pyrimidinecarbonitrile derivative. Treatment of the latter derivative with a solution of water and ethanol containing an excess of potassium hydroxide and hydrogen sulphide at about 20° to 40° C. for about 20 to 30 hours gives the corresponding compound of formula I in which $R^2$ is thioxo.

The following examples illustrate further this invention.

EXAMPLE 1

1,4-Dihydro-6-(ethylamino)-2-methyl-4-oxo-5-pyrimidinecarbonitrile (I: $R^1$=Me, $R^2$=O, $R^3$=H and $R^4$=Et)

To a suspension of 2-cyano-3,3-bis(methylthio)-2-propenoic acid, methyl ester (8.12 g, 1 eq) in dimethoxyethane (14 mL) was added a solution of ethylamine (2.16 g, 1.2 eq.) in dimethoxyethane (6.5 mL). The suspension turned to solution, and a white solid began to precipitate. After about 10 min the solvent was removed and the residue was filtered with diethyl ether to yield 2-cyano-3-ethylamino-3-methylthio-2-propenoic acid, methyl ester (7.2 g): mp 86°–88° C.

To a solution of acetamidine hydrochloride (0.83 g, 1.1 eq) in DMF (5.5 mL) was added postassium carbonate (1.22 g, 2.2 eq) and the mixture was stirred at room temperature for about 10 min. The above cyanoester (1.6 g, 1 eq) was added and the mixture was heated to 90° C. overnight. The reaction mixture was cooled, diluted with water and filtered to give a solid (0.3 g). Further concentration to dryness followed by filtration of residue with small amount of water gave more solid (0.8 g). The two solids were pooled and crystallized from methanol to give the title compound (0.6 g): mp>290° C.; Anal. Calcd. for $C_8H_{10}N_4O$: C, 53.93% H, 5.61% N, 31.46% and Found: C, 53.67% H, 5.83% N, 31.31%, IR (mineral oil) 3300, 2800, 2220, 1650 $cm^{-1}$; UV max (MeOH) 289 nm ($\epsilon$6140), 268 (5240), 226 (40,100); NMR (DMSO-$d_6$) $\delta$ 7.75 (t, 1H), 3.4 (m, 2H), 2.23 (s, 3H), 1.1 (s, 3H).

Similarly, the following compounds of formula I can be prepared: 1,4-dihydro-6-(butylamino)-2-cyclohexyl-4-oxo-5-pyrimidinecarbonitrile, 1,4-dihydro-6-(diethylamino)-2-butyl-4-oxo-5-pyrimidinecarbonitrile, 1,4-dihydro-6-(N-methyl-N-propylamino)-2-benzyl-4-oxo-5-pyrimidinecarbonitrile, and 1,4-dihydro-6-(propylamino)-2-cyclopropyl-4-oxo-5-pyrimidinecarbonitrile.

EXAMPLE 2

Test for Cardiotonic Activity in Isolated Cat Papillary Muscle

A cat of either sex was anesthetized with Na pentobarbital, 25–30 mg/kg i.v. The heart was rapidly removed and placed in cool Tyrode's solution which had been equilibrated with 95% $O_2$-5% $CO_2$. The right ventricle was opened by cutting down the sides and around the apex so that the free wall could be folded back on the atrioventricular groove. Usually at least three suitably-sized papillary muscles were found (1 mm or less in thickness). Threads were tied around the chordae tendonae and the base of the muscle just above its point of insertion into the ventricular wall. The chordae were cut, and the muscle was removed along with a small button of ventricular wall. If a sufficient number of papillary muscles were not present, trabeculae carnae could also be used. The best ones were usually found inserting just under the valve.

The preparations were mounted in tissue baths containing Tyrode's solution at 37° C. bubbled with 95% $O_2$-5% $CO_2$. One thread was affixed to a tissue holder incorporating a pair of platinum electrodes and the other thread was attached to a force displacement transducer. Initial tension placed on the preparation was 0.2 g (less for very small muscles). The preparations were stimulated with square-wave pulses, 2–4 msec. in duration and 10% above threshold voltage, at a rate of 0.5 Hz. The muscles were then gently and gradually stretched to their optimum force-length relation (at which twitch tension was maximal-further stretching did not result in any further increase in the overall magnitude of the twitch). The preparations were then allowed to equilibrate for one hour with frequent changes of the bathing fluid (10–15 min intervals). The test compound was added to the bath in 0.1 ml of vehicle and incubated with the preparation for 15 min or until peak effect was attained.

Using this method, the following representative compound of formula I was effective for incresing the force of contraction of the papillary muscle (the amount of test compound in the bath and increase in contractility is given in the parenthesis): 1,4-dihydro-6-(ethylamino)-2-methyl-4-oxo-5-pyrimidinecarbonitrile (at $10^{-4}$ molar increased contactility by 88%).

EXAMPLE 3

Pentobarbital-induced Cardiac Failure in the Dog

A dog of either sex was anesthetized with Na pentobarbital, 30–35 mg/kg i.v. The trachea was intubated and the animal was respired at a rate of 20 breaths/min (stroke volume=14 cc/kg.). Both femoral veins were cannulated. One cannula was used for infusion of pentobarbital to induce and maintain failure, the other for injection of test compounds. A cannula was inserted into the aorta via a femoral artery and the cannula was attached to a blood pressure transducer for measurement of systolic, diastolic and mean aortic blood pressure. A millar pressure-tip catheter was inserted into the other femoral artery and advanced into the left ventricle to record intraventricular pressure and dP/dt. Subdermal needle electrodes were used to record a lead II electrocardiogram and heart rate.

Following a stabilization period of at least 30 min, experimental failure was induced by the i.v. infusion of Na pentobarbital, 0.75 mg/kg/min in 0.2 ml of saline/min, until a 40–50% decrease in peak positive dP/dt was obtained. The failure state was maintained at this level throughout the experiment by continuous infusion of Na pentobarbital, 0.11–0.15 mg/kg/min. Once the maintenance infusion was started, at least 15 min were allowed to elapse before test drugs were administered.

Test compounds were prepared in N saline. Increasingly higher doses were given i.v. at 30 min-1 hr intervals in order to determine a therapeutic (50% increase in dP/dt) to toxic (appearance of arrhythmias) ratio where possible.

Using this method, the following representative compound of formula I was effective for increasing the cardiac contractility of the heart (the amount of test compound in mg per kg of body weight administered i.v. to give a 50% increase in dP/dt is given in the parenthesis): 1,4-dihydro-6-(ethylamino)-2-methyl-4-oxo-5-pyrimidinecarbonitrile (0.02 mg/kg).

We claim:

1. A method of increasing cardiac contractility in a mammal, which comprises administering to the mammal in need thereof an effective cardiotonic amount of a compound of the formula

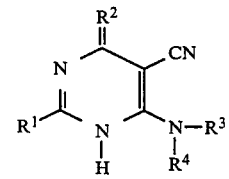

in which $R^1$ is lower alkyl, cyclo(lower)alkyl or benzyl; $R^2$ is oxo or thioxo; $R^3$ is hydrogen or lower alkyl; and $R^4$ is lower alkyl; or a therapeutically acceptable addition salt thereof.

2. The method of claim 1 wherein $R^1$ is lower alkyl, cyclo(lower)alkyl or benzyl; $R^2$ is oxo, $R^3$ is hydrogen, and R[4] is lower alkyl; or a therapeutically acceptable addition salt thereof.

3. The method of claim 1 wherein said compound is 1,4-dihydro-6-(ethylamino)-2-methyl-4-oxo-5-pyrimidinecarbonitrile.

4. A cardiotonic pharmaceutical composition, which comprises a cardiotonic effective amount of a compound of the formula

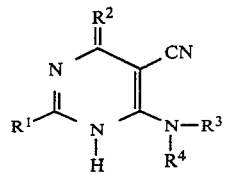
(I)

in which R[1] is lower alkyl, cyclo(lower)alkyl or benzyl; R[2] is oxo or thioxo; R[3] is hydrogen or lower alkyl; and R[4] is lower alkyl; or a therapeutically acceptable addition salt thereof, and a pharmaceutically acceptable carrier therefor.

5. The cardiotonic pharmaceutical composition of claim 4 wherein R[1] is lower alkyl, cyclo(lower)alkyl or benzyl; R[2] is oxo; R[3] is hydrogen; and R[4] is lower alkyl.

6. The cardiotonic pharmaceutical composition of claim 4 wherein said compound is 1,4-dihydro-6-(ethylamino)-2-methyl-4-oxo-5-methyl-5-pyrimidinecarbonitrile.

* * * * *